(12) United States Patent
Chinn et al.

(10) Patent No.: US 6,300,143 B1
(45) Date of Patent: Oct. 9, 2001

(54) ELECTROCHEMILUMINESCENT ASSAYS FOR EUKARYOTIC CELLS

(75) Inventors: Paul Chinn, Vista; Michael J. LaBarre, San Diego, both of CA (US)

(73) Assignee: IDEC Pharmaceuticals Corporation, San Diego, CA (US)

( * ) Notice: Subject to any disclaimer, the term of this patent is extended or adjusted under 35 U.S.C. 154(b) by 0 days.

(21) Appl. No.: 09/259,347

(22) Filed: Mar. 1, 1999

(51) Int. Cl.[7] .................................................. G01N 33/553
(52) U.S. Cl. ........................ 436/526; 436/518; 436/501; 436/524; 436/546; 436/172; 435/4; 435/7.1; 435/7.21; 435/7.22; 435/7.31; 435/7.93
(58) Field of Search ..................................... 436/526, 518, 436/524, 501, 546, 172; 435/4, 7.1, 7.21, 7.22, 7.31, 7.93

(56) References Cited

U.S. PATENT DOCUMENTS

| | | | |
|---|---|---|---|
| 4,280,815 | * | 7/1981 | Oberhardt et al. ...................... 23/230 |
| 4,476,230 | * | 10/1984 | Sieber ................................... 436/507 |
| 5,453,356 | * | 9/1995 | Bard et al. ................................. 435/6 |
| 5,527,710 | * | 6/1996 | Nacamulli et al. ................... 436/517 |
| 5,541,113 | * | 7/1996 | Siddigi et al. ........................... 436/56 |
| 5,679,519 | * | 10/1997 | Oprandy .................................... 435/6 |
| 5,705,402 | * | 1/1998 | Leland et al. ......................... 436/526 |
| 5,716,781 | * | 2/1998 | Massey et al. ............................ 435/6 |
| 5,744,367 | * | 4/1998 | Talley et al. ........................... 436/172 |
| 5,804,400 | * | 9/1998 | Martin et al. ........................... 435/18 |
| 5,858,676 | * | 1/1999 | Yang et al. ............................... 435/6 |
| 5,945,344 | * | 8/1999 | Hayes et al. .......................... 436/172 |
| 5,958,783 | * | 9/1999 | Josel et al. ............................. 436/84 |
| 5,976,887 | * | 11/1999 | Bruno et al. ............................ 436/80 |
| 5,981,286 | * | 11/1999 | Herrmann et al. ...................... 436/84 |
| 6,009,760 | * | 8/2000 | Jameison et al. ..................... 252/700 |
| 6,066,448 | * | 5/2000 | Wohlstadter et al. .................... 435/6 |

OTHER PUBLICATIONS

Grimshaw et al, "Development of equilibrium immunoassay using electrochemiluminescent detection . . . development", J. Pharmaceutical and Biomedical Analysis, 16:605–612, 1997.

Yu et al, "Immunomagnetic–electrochemiluminescent detection of *Escherichia coli* 0157 and *Salmonella typhimurium* . . . samples", Appl. and Envir. Microbiol., 62(2):587–592, 1996.

Deaver, "A new non–isotopic detection system for immunoassays", Nature, 377:758–760, 1995.

Gatto–Menking et al, "Sensitive detection of biotoxoids and bacterial spores using an immunomagnetic electrochemiluminescence sensor", Biosensors & Bioelectronics, 10:501–507, 1995.

Abraham et al, "Determination of binding constants of diabodies directed against prostate–specific antigen using electrochemiluminescence–based immunoassays", J. of Molecular Recognition, 9:456–461, 1996.

Yang et al, "Electrochemiluminescence: A new diagnostic and research tool", Bio/Technology, 12:193–194, 1994.

Blackburn et al, "Electrochemiluminescence detection for development of immunoassays and DNA probe assays for clinical diagnostics", Clinical Chemistry, 37(9):1534–1539, 1991.

Glaser, "Expose yourself to Origen technology: a high performance research tool", Nature Biotechnology, 14(3):259–260, 1996.

* cited by examiner

*Primary Examiner*—Long V. Le
*Assistant Examiner*—Pensee T. Do
(74) *Attorney, Agent, or Firm*—Robin L. Teskin

(57) ABSTRACT

Disclosed are immunomagnetic electrochemiluminescence assays for eukaryotic cells, particularly human cells. A competitive binding assay is disclosed which enables affinity measurements of antibodies specific for eukaryotic cell membrane proteins. Such an assay is particularly useful for verifying or measuring the affinity of therapeutic antibodies following chelate conjugation.

10 Claims, 1 Drawing Sheet

Figure 1:
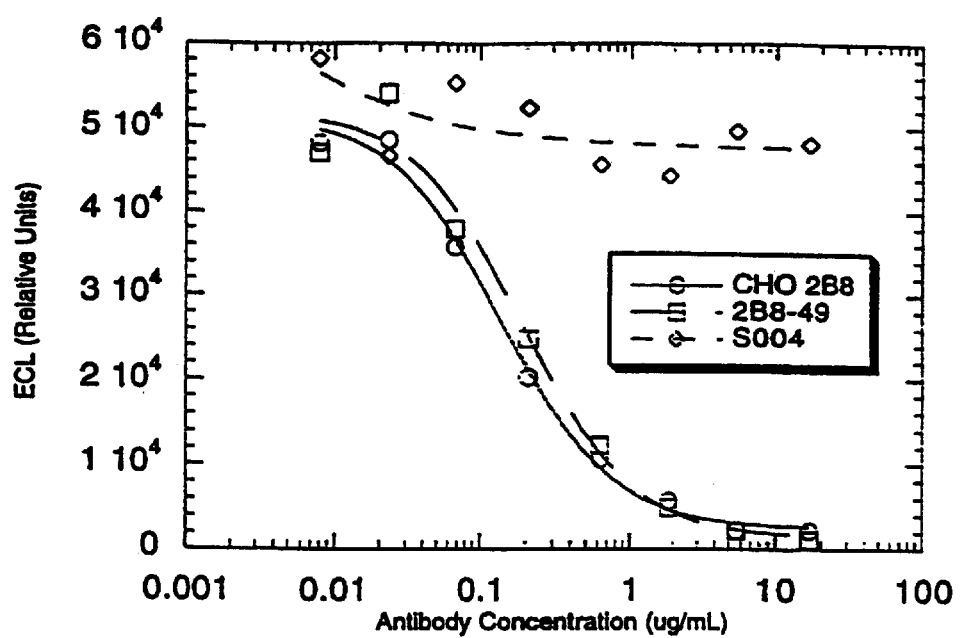

Competitive Binding of CHO-Derived 2B8 to CD20-Positive Human Cells

Competitive Binding of CHO-Derived 2B8 to CD20-Positive Human Cells

ELECTROCHEMILUMINESCENT ASSAYS FOR EUKARYOTIC CELLS

1. FIELD OF THE INVENTION

The present invention relates to the use of electrochemiluminescence instrumentation for the detection of and quantitation of binding to membrane-bound antigens on the surface of eukaryotic cells.

2. TECHNOLOGY BACKGROUND

All publications and patent applications herein are incorporated by reference to the same extent as if each individual publication or patent application was specifically and individually indicated to be incorporated by reference.

Electrochemiluminescence is a technology having broad application in the fields of diagnostics, drug discovery and basic research. The technology has particular utility in the design of immunoassays, which benefit from increased sensitivity, dynamic range, kinetics and format flexibility by electrochemiluminescence technology. In particular, incubation times may be significantly reduced, due to the solution phase kinetics used and the elimination of wash steps (1).

Electrochemiluminescence is the process by which light generation occurs when low voltage is applied to an electrode, triggering a cyclical oxidation and reduction reaction of a heavy metal ion, such as ruthenium. The heavy metal ion is bound in a chelate of tris-bipyridine (i.e., $Ru(bpy)_3^{2+}$). A second reaction component is an electron carrier, such as tripropylamine (TPA), which mediates the redox reaction. This electron carrier is present in excess, and is consumed during the assay while the heavy metal chelate is recycled. Because the metal chelate is recycled and the carrier is present in excess, the signal generated from the assay is intensified (1, 2).

The luminescent reaction is triggered upon application of an electric potential. There are currently several instruments available on the market designed to deliver the necessary voltage and quantify the resulting signal. These products include ORIGEN® (Igen Corp.) and QPCR System 5000® (Perkin-Elmer Corp.) magnetic electrochemiluminescence detectors (2). The ORIGEN® instrument operates using magnetic beads which have been designed to interact with or bind to the antigen of interest. The beads are added to the reaction tubes and the tubes are placed in a vortexing carousel which keeps the beads in suspension prior to sampling. An automatic sample delivery system aspirates a user-determined volume of each reaction mixture and pumps it into the flow cell. As the sample is pumped through the cell the magnetic beads are captured by a magnet onto a platinum electrode which delivers the required electric potential. The light subsequently emitted is measured in a photomultiplier tube and digitally recorded. The cell is then washed in preparation for the next reading (1).

In recent years, many papers have been published reporting the success of magnetic electrochemiluminescent techniques in the detection and quantitation of various targets, including bacteria (3), biotoxoids and bacterial spores (2), specific antigens and macromolecules (4–6), and nucleic acids (5, 7). However, no assays or diagnostic applications have been reported which apply immunomagnetic electrochemiluminescence (IM-ECL) to eukaryotic cells. Yu and Bruno suggest that IM-ECL technology is broadly applicable, even to eukaryotic cells, and make reference to an early publication by researchers at Igen Corporation (3). However, a review of the referenced publication reveals no such disclosed use (5). Moreover, there are no other reports of such a use in the literature.

The absence of reported IM-ECL assays using eukaryotic cells is probably due to the vortexing step typically employed by IM-ECL instruments which keeps the samples in suspension until an aliquot is aspirated for quantitation. Although IM-ECL technology has been used to detect bacterial cells (3), it has long been presumed by those of skill in the art that eukaryotic cells, and in particular animal cells, were simply too fragile to be used in such assays.

The present inventors have surprisingly found that IM-ECL instrumentation may be employed to conduct immunoassays wherein eukaryotic cells are targeted. This discovery allows further expansion of this helpful technology to cover new assay formats, and should be applicable to all assay types, including competitive assays and detection/diagnostic techniques.

3. SUMMARY OF THE INVENTION

The present invention encompasses immunoassays and other types of diagnostic tests to be performed on eukaryotic cells using an immunomagnetic electrochemiluminescence instrument. Particularly included are competitive binding assays designed to measure affinity of a ligand for an antigen bound to or displayed on the surface of a eukaryotic cell, diagnostic assays aimed at detection of particular antigens, and drug discovery protocols.

4. BRIEF DESCRIPTION OF THE DRAWINGS

FIG. 1. The immunoreactivity of CHO-derived 2B8 was compared to the 2B8-49 parent antibody produced in a hybridoma cell line by direct competition in an ORIGEN assay. Increasing amounts of antibody was incubated with a fixed concentration of CD20-positive B-cells (SB) and a trace amount of ruthenium-labeled CHO 2B8. After incubation for three hours at ambient temperature, binding, expressed as relative electrochemiluminescence (ECL), was determined using the ORIGEN instrument as described in the Materials and Methods. Values represent the means of duplicate determinations. Average affinity constants for CHO 2B8 and 2B8-49 were calculated to be $1.3 \times 10^{-10}$ M and $2.5 \times 10^{-10}$ M, respectively. An irrelevant isotype antibody (S004), was included for comparison.

5. DETAILED DESCRIPTION OF THE INVENTION

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The present invention encompasses a multitude eukaryotic cell-based assays using IM-ECL, including a method for measuring average affinity of a test antibody to a eukaryotic cell membrane antigen comprising (a) labeling a control antibody with a metal ion chelate, said control antibody having the same target specificity as said test antibody; (b) incubating varying amounts of said test antibody with (i) a trace amount of said labeled control antibody, (ii) a quantity of eukaryotic cells expressing said membrane antigen, (iii) a suitable electron carrier, and (iv) a quantity of paramagnetic beads having a binding specificity for said cells; (c) determining the quantity of binding in each sample tube based on relative electrochemilurninescence using an immunomagnetic electrochemiluminescence instrument; and (d) calculating the average affinity value of the test antibody.

Eukaryotic cells which may be used in the disclosed assays includes animal cells. The invention will find particular use in assays designed for human cells, especially in the field of diagnostics and drug design. Said eukaryotic cells may be fresh, reconstituted from a lyophilized sample, or fixed. It should be apparent to those of skill in the art that any exposed antigen on the surface of the cell may be targeted by either the test and control antibodies or the magnetic beads, and that such antigen need not be normally expressed on the cell surface if it is possible to express said antigen using recombinant DNA techniques. In fact, the assay may even be used for membrane fusion proteins engineered to display a particular antigenic epitope on the cell surface (for instance, see U.S. Patents Yang U.S. Pat. No. 5,665,590 and Coruzzi et al. U.S. Pat. No. 5,824,867 herein incorporated by reference).

Any metal ion chelate may be used to label the control antibody, so long as the chelate is recyclable and capable of being used in an immunomagnetic electrochemiluminescence instrument. Ruthenium is particularly preferred, in the form of a $Ru(bpy)_3^{2+}$ chelate. Similarly, any electron carrier may be used. A particularly preferred carrier is tripropylamine (TPA). However, other metal chelates and carriers are known which may also be used for ECL (7).

The beads are designed with binding specificity for said cells such that they mediate transfer of said cells to the magnet contained in the ECL instrument, such that an electric potential may be applied. Although it is possible for the beads to have the same binding specificity for the cells as do the test and control antibody, it is preferable for the beads to have an alternative binding specificity so as not to interfere in any way with the affinity measurement.

The test antibody may be any antibody of interest for which it is desirable to measure affinity to the target antigen. The affinity of other types of proteins, such as receptor ligands, may also be tested. The present inventors have found that the assay is particularly suitable for measuring the affinity of therapeutic and diagnostic antibodies which have been conjugated to chelates designed to facilitate conjugation to radioactive isotopes. Antibodies labeled with radioactive isotopes used for therapeutic purposes such as the treatment of cancer, i.e., beta emitters such as yttrium-[90], may be particularly suitable for the disclosed assays. Such radiolabels tend to be highly radiolytic and may jeopardize antibody integrity and the efficacy of treatment. Thus, it would be highly beneficial to be able to quickly and accurately verify the affinity of the chelate-conjugated antibody before it is radiolabeled and subsequently administered to a patient.

It should be apparent to those of skill in the art that the novelty of the invention is the finding that eukaryotic cells are amenable to assays performed using an IM-ECL device. Accordingly, any known assay format may be designed for such applications. For instance, also encompassed in the present invention is a method for detecting an antigen on the surface of a eukaryotic cell comprising (a) incubating said cell with paramagnetic beads having binding affinity for said cell and a quantity of ligand labeled with a metal ion chelate, said ligand having a binding specificity for said cell, and (b) detecting a binding interaction between said beads, said cell and said labeled ligand using an immunomagnetic-cherniluminescent instrument. Of course, said ligand may be an antibody as described above. All other specific variations applicable to the competitive binding assay are applicable to detection assays as well.

Also encompassed are sandwich type assays where the ligand itself is not labeled, but a secondary ligand or antibody is labeled with a heavy metal ion chelate which is specific for the bound ligand. For instance, the invention encompasses a method for detecting an antigen on the surface of a eukaryotic cell comprising (a) incubating said cell with (i) para-magnetic beads having binding affinity for said cell, (ii) a ligand having an alternative binding specificity for said cell, and (iii) a ruthenium-labeled antibody having an alternative specificity for said ligand, and (b) detecting a binding interaction between said beads, said cell, said ligand and said ruthenium-labeled antibody using an immunomagnetic-chemiluminescent instrument.

EXAMPLE 1

Immunoreactivities of an anti-CD20 antibody, 2B8, and its chelate-conjugated derivative, 2B8-MX-DTPA, were determined by competitive binding to CD20-positive SB cells using the ORIGEN® electrochemiluminescent method (8). Antibody 2B8 is the subject of copending applications Ser. Nos. 08/475,813, 08/475,815 and 08/478,967, herein incorporated by reference in their entirety, which disclose radiolabeled anti-CD20 conjugates for diagnostic "imaging" of B cell lymphoma tumors and therapeutic radiolabeled antibodies for the treatment of B cell lymphoma.

MX-DTPA (diethylenetriarninepentaacetic acid) is a bifunctional chelator, which comprises a 1:1 mixture of 1-isothiocyanatobenzyl-3-methyl-DTPA and 1-methyl-3-isothiocyanatobenzyl-DTPA. Patents relating to chelators and chelator conjugates are known in the art. For instance, U.S. Pat. No. 4,831,175 of Gansow is directed to polysubstituted diethylenetriaminepentaacetic acid chelates and protein conjugates containing the same, and methods for their preparation. U.S. Pat. Nos. 5,099,069, 5,246,692, 5,286,850, and 5,124,471 of Gansow also relate to polysubstituted DTPA chelates. These patents are incorporated herein in their entirety.

CD20 is expressed during early pre-B cell development and remains until plasma cell differentiation. Specifically, the CD20 molecule may regulate a step in the activation process which is required for cell cycle initiation and differentiation and is usually expressed at very high levels on neoplastic ("tumor") B cells. CD20, by definition, is present on both "normal" B cells as well as "malignant" B cells, i.e., those B cells whose unabated proliferation can lead to B cell lymphoma. Thus, the CD20 surface antigen has the potential of serving as a candidate for "targeting" of B cell lymphomas.

The following methods were performed:

Log-phase SB cells (ATCC #CCL 120) were harvested from culture and washed twice with 1X HBSS. Cells were diluted in IX PBS pH 7.2 containing 1% (w/v) bovine serum albumin. In some experiments, lyophilized cells were used after reconstitution with sterile water.

Ruthenium-labeled tracer antibody was prepared by incubating CHO-derived 2B8 (lot #165) in 1X PBS, pH 7.2 with the N-hydroxysuccinimide ester of ruthenium (II) trisbipyridine chelate (TAG-NHS) at a 15:1 molar ratio of TAG-NHS to antibody. After 1 h incubation at ambient temperature, protected from light, the reaction was quenched with glycine for 10 min. Unreacted TAG was removed by size exclusion chromatography using a Pharmacia PD-10 column equilibrated with 1×PBS. Protein concentration was determined using the Bradford protein assay. TAG incorporation was determined by measuring absorbance at 455 nm. The molar ratio of TAG to protein was calculated to be 3.0.

Assays were performed in 12×75 mm polypropylene tubes. Varying amounts of competing antibody (0.002–17 ug/mL) were incubated in 1×PBS, pH 7.2, containing 1% (w/v) BSA with 0.08 ug/mL TAG-labeled CHO 2B8, 0.08 mg/mL anti-CD19 beads, and 167,000 cells/ml. After incubation at ambient temperature with orbital mixing for 3 h, relative electrochemiluminescence (ECL) was determined using the ORIGEN instrument. Mean ECL values were determined for duplicated samples and plotted vs. competing antibody concentration using Kaleidagraph software. For some experiments, per cent inhibition was plotted. Competition curves were fitted and EC 50 values (antibody concentration giving 50% maximal binding) determined using the following 4-parameter program:

$$y=((m1-m4)/(1+(m0/m3)\hat{0}m2))+m4; m1=; m2=; m3=; m4=$$

m0=independent variable m1=zero signal response in relative ECL units m2=curvature parameter m3=EC50 in ug/mL m4=maximum signal response in relative ECL units Average affinity values were calculated from EC50 values and the known concentration of trace antibody using the method of Muller (9).

Results showed that CHO 2B8 inhibits binding to CD20-positive cells to the same extent as 2B8 antibody derived from hollow-fiber bioreactors (2B8–49) (FIG. 1). The EC50 values were determined graphically and the method of Muller (1980) used to calculate average affinity values. The affinity for CHO 2B8 was determined to be $1.3 \times 10^{-10}$ M; the 2B8 antibody derived from hollow-fiber bioreactors gave an affinity value of $2.5\ 10^{-10}$ M. Non-specific binding was negligible as demonstrated by the lack of competition with the irrelevant isotype antibody, S004.

References

1. IGEN, website http://www.igen.com/htdocs/origtech.htm.
2. Gatto-Menking, D. L., Yu, H., Bruno, J. G., Goode, M. T., Miller, M. and Zulich, A. W. 1995. Sensitive detection of biotoxoids and bacterial spores using an immunomagnetic electrochemiluminescence sensor. Biosensors & Bioelectronics 10: 501–507.
3. Yu, H. and Bruno, J. G. 1996. Immunomagnetic-electrochemiluminescent detection of *Escherichia coli* 0157 and *Salmonella typhimurium* in foods and environmental water samples. Appl. Environment. Microbiol. 62(2): 587–592.
4. Abraham, R., Buxbaum, S., Link, J., Smith, R., Venti, C. and Darsley, M. 1996. Determination of binding constants of diabodies directed against prostate specific antigen using electrochemiluminescence-based immunoassays. J. Mol. Recognition 9: 456–461.
5. Blackburn, G. P., Shah, H. P., Kenten, J. H., Leland, J., Kamin, R. A., Link, J., Peterman, J., Powell, M. J., Shah, A., Talley, D. B., Tyagi, S. K., Wilkins, E., Wu, T. -G. and Massey, R. J. 1991. Electrochemiluminescence detection for development of immunoassays and DNA probe assays for clinical diagnostics. Clin. Chem. 37(9): 1534–1539.
6. Kibbey, M. C. and Olson, C. March, 1996. Expose yourself to ORIGEN® technology; A high performance research tool. Nature Biotech. 14(3): 259–260.
7. Yang, H., Leland, J. K., Yost, D., Massey, R. J. February 1994. Electrochemiluminescence: A new diagnostic and research tool. Biotechnol. 12: 193–194.
8. Leland, J. K. and Powell, M. J. J. (1990) Electrochem. Soc. 137, 3127.
9. Muller, R. J. Immunological Methods (1980) 34, 345.

What is claimed:

1. A method for measuring average affinity of a test antibody to a eukaryotic cell membrane antigen comprising:

(a) labeling a control antibody with a metal ion chelate, said control antibody having the same target specificity as said test antibody;

(b) incubating in two or more sample tubes varying amounts of said test antibody with (i) a trace amount of said labeled control antibody, (ii) a quantity of eukaryotic cells expressing said membrane antigen, (iii) a suitable electron carrier and (iv) a quantity of paramagnetic beads having a binding specificity for said cells;

(c) determining the quantity of binding in each sample tube based on relative electrochemiluminescence using an immunomagnetic electrochemiluminescence instrument; and (d) calculating the average affinity value of the test antibody.

2. The method of claim 1, wherein said test antibody has been conjugated to a bifunctional chelator.

3. The method of claim 1, wherein said metal ion is ruthenium.

4. The method of claim 1, wherein said electron carrier is tripropylamine.

5. The method of claim 1, wherein said eukaryotic cells are B cells.

6. The method of claim 1, wherein said test antibody is an anti-CD20 antibody.

7. The method of claim 6, wherein said para-magnetic beads display an anti-CD19 antibody.

8. The method of claim 1, wherein said average affinity is calculated using EC50 value.

9. The method of claim 1, wherein said membrane antigen is encoded by a recombinant DNA.

10. The method of claim 1, wherein said eukaryotic cells are fresh, reconstituted from a lyophilized sample, or fixed.

* * * * *